(12) United States Patent
Hladio et al.

(10) Patent No.: US 11,176,667 B2
(45) Date of Patent: Nov. 16, 2021

(54) SYSTEMS, DEVICES AND METHODS FOR BONE REORIENTATION

(71) Applicant: INTELLIJOINT SURGICAL INC., Kitchener (CA)

(72) Inventors: Andre Novomir Hladio, Waterloo (CA); Joseph Arthur Schipper, Kitchener (CA); Justin Aaron Michael, North Vancouver (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 115 days.

(21) Appl. No.: 16/741,963

(22) Filed: Jan. 14, 2020

(65) Prior Publication Data

US 2020/0226753 A1 Jul. 16, 2020

Related U.S. Application Data

(60) Provisional application No. 62/792,529, filed on Jan. 15, 2019.

(51) Int. Cl.
| | |
|---|---|
| *G06K 9/00* | (2006.01) |
| *A61B 5/05* | (2021.01) |
| *G06T 7/00* | (2017.01) |
| *A61B 34/20* | (2016.01) |
| *A61B 34/10* | (2016.01) |
| *G06T 7/73* | (2017.01) |

(52) U.S. Cl.
CPC ............ *G06T 7/0012* (2013.01); *A61B 34/10* (2016.02); *A61B 34/20* (2016.02); *G06T 7/75* (2017.01); *A61B 2034/105* (2016.02); *A61B 2034/2055* (2016.02); *G06T 2200/04* (2013.01); *G06T 2207/30008* (2013.01)

(58) Field of Classification Search
USPC ....... 382/100, 103, 106, 128–132, 154, 162, 382/168, 173, 181, 199, 209, 214, 219, 382/254, 274, 276, 285–291, 305, 321; 606/130; 128/849; 600/409, 587
See application file for complete search history.

(56) References Cited

U.S. PATENT DOCUMENTS

| | | | |
|---|---|---|---|
| 2014/0031722 A1* | 1/2014 | Li | A61B 5/1077 600/587 |
| 2014/0052149 A1* | 2/2014 | van der Walt | A61F 2/4609 606/130 |

(Continued)

*Primary Examiner* — Seyed H Azarian (57) ABSTRACT

There is provided a system for assisting a bone reorientation that includes (or communicates with) localization system components comprising a reference element to mount to the patient's bone and a tracker element to mounting to a bone fragment; and at least one computing unit coupled to the localization system components. The computing unit is configured to: define change in bone fragment orientation data (CBFOD) responsive to tracking measurements received from the localization system components; receive mapping information (e.g. generated from a pre-operative medical image of the patient's bone and bone fragment region) to define a map between the CBFOD and clinical parameters; and calculate and provide for display one or more clinical parameters based on the CBFOD and the map. A tracker element coupling component is also described with quick-connect and adjustment features. Method and other aspects are provided.

21 Claims, 6 Drawing Sheets

(56) References Cited

U.S. PATENT DOCUMENTS

| | | | |
|---|---|---|---|
| 2014/0261456 A1* | 9/2014 | Malackowski | A61B 46/10 128/849 |
| 2016/0157751 A1* | 6/2016 | Mahfouz | A61B 5/062 600/409 |
| 2017/0224422 A1* | 8/2017 | Bakirtzian | A61B 5/1127 |
| 2021/0106386 A1* | 4/2021 | Lang | A61B 34/74 |

\* cited by examiner

SYSTEMS, DEVICES AND METHODS FOR BONE REORIENTATION

FIELD

The present disclosure relates to computer-assisted procedures for patients and more particularly to systems, devices and methods for bone reorientation, for example, to provide computer assistance to reorient a bone fragment.

BACKGROUND

Peri-acetabular osteotomy (PAO) is a surgical technique to treat hip dysplasia, a disorder in which the acetabulum is too shallow, resulting in poor biomechanics of the hip. PAO involves cutting the pelvis to free a bone fragment containing the acetabulum, rotating the freed bone fragment, and re-attaching it to the pelvis in order to improve the biomechanics of the patient's hip. Clinical metrics of acetabular shape and orientation are typically measured using x-ray images based on anatomic landmarks and/or radiographic features, with those same metrics used to define desired surgical outcomes.

Current surgical techniques involve moving this fragment intra-operatively to a visually estimated position, installing temporary fixation, often screws or k-wires, and verifying the position using intra-operative c-arm. Intra-operative radiographs are assessed to determine the acceptability of the fragment position using standard clinical measurements. Frequently, the fragment is not in an acceptable position, and must be moved by removing the temporary fixation, adjusting the fragment position, installing new fixation, and capturing an updated radiograph. This guess-and-check process can be repeated as many as five times before the correct fragment position is attained. When correct position is confirmed, the temporary fixation is replaced with final fixation.

This process of intra-operative fluoroscopy guidance process can lead to a number of undesirable outcomes. The repeated installation of temporary fixation can lead to higher levels of bone loss from repeated drilling, which can result in poor final fixation. The repeated c-arm shots lead to higher radiation exposure for the patient and surgical staff, the risks of which are well documented. Furthermore, the time required to attain proper fragment positioning increases the cost of the surgery via operating room costs and staff costs, and is also associated with an increased risk of infection. Lastly, the 2D nature of fluoroscopy results in incomplete information regarding fragment orientation that requires careful, and potentially error prone, use of clinical judgement to interpret.

There are also other orthopedic surgeries in which a bone fragment is removed from a primary bone, rotated to a desired position, and affixed back to the surrounding bone, such as Extended Trochanteric Osteotomies (ETOs).

SUMMARY

There is provided a system for assisting a bone reorientation that includes (or communicates with) localization system components comprising a reference element to mount to the patient's bone and a tracker element to mounting to a bone fragment; and at least one computing unit coupled to the localization system components. The computing unit is configured to: define change in bone fragment orientation data (CBFOD) responsive to tracking measurements received from the localization system components; receive mapping information (e.g. generated from a pre-operative medical image of the patient's bone and bone fragment region) to define a map between the CBFOD and clinical parameters; and calculate and provide for display one or more clinical parameters based on the CBFOD and the map. A tracker element coupling component is also described with quick-connect and adjustment features. Method and other aspects are provided.

There is provided, in a first aspect, a system to perform a bone reorientation on a patient comprising: localization system components comprising a reference element to mount to the patient's bone and a tracker element to mount to a bone fragment; and at least one computing unit coupled to the localization system components and configured to: define change in bone fragment orientation data (CBFOD) responsive to tracking measurements received from the localization system components; receive mapping information to define a map between the CBFOD and clinical parameters; wherein the CBFOD and the mapping information are with respect to corresponding frames of reference; and wherein the mapping information is generated from a pre-operative medical image of the patient's bone and bone fragment region; and calculate and provide for display one or more clinical parameters based on the CBFOD and the map.

There is provided, in a second aspect, a system to perform a bone reorientation on a patient comprising: a computing unit coupled to a localization system, the computing unit configured to calculate and provide for display clinical parameters based on received CBFOD from the localization system; wherein the localization system comprises localization system components comprising a reference element to mount to the patient's bone and a tracker element to mount to a bone fragment.

There is provided in a third aspect, a computer-implemented method to perform a bone reorientation on a patient comprising: defining, by a processing unit, change in bone fragment orientation data (CBFOD) responsive to tracking measurements received by the processing unit from localization system components comprising a reference element configured to mount to the patient's bone and a tracker element configured to mount to a bone fragment; receiving, by the processing unit, mapping information to define a map between the CBFOD and clinical parameters; wherein the CBFOD and the mapping information are with respect to corresponding frames of reference; and wherein the mapping information is generated from a pre-operative medical image of the patient's bone and bone fragment region; and calculating and providing for display, by the processing unit, one or more clinical parameters based on the CBFOD and the map.

There is provided in a fourth aspect a method to perform a bone reorientation on a patient comprising, by a processing unit: calculating and providing for display clinical parameters based on received CBFOD from a localization system, the localization system comprising localization system components including a reference element configured to mount to the patient's bone and a tracker element configured to mount to a bone fragment.

These and other aspects will be apparent to a person of ordinary skill in the art.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light. More than one inventive concept may be shown and described and each may stand-alone or be combined with one or more others unless stated otherwise.

DETAILED DESCRIPTION

There is described a method of intra-operative navigation of the fragment orientation which will reduce the number of trials required to reach an acceptable fragment position, reduce the health risks and monetary costs associated with repeated fragment repositioning and simplify interpretation of the positional feedback provided to the surgeon.

Figure 1:
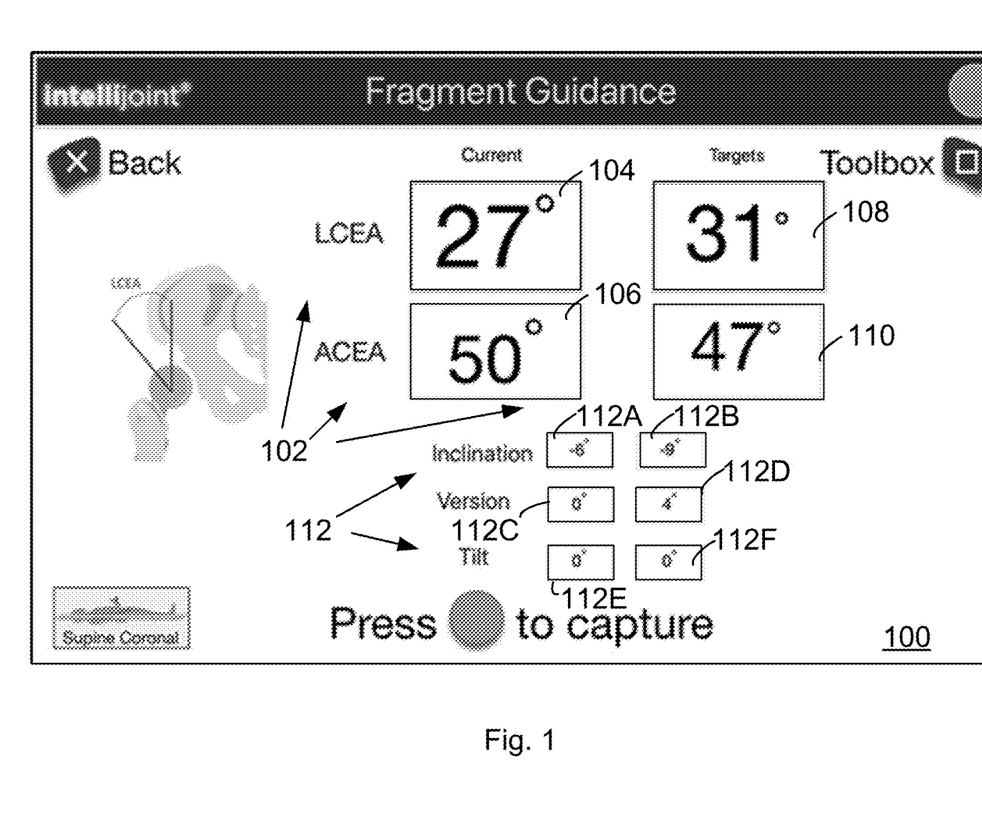
FIG. 1 is an illustration of a screen shot showing clinical parameters for a procedure.

The system comprises two primary aspects, a localization system with a reference element mounted to the patient's bone and a tracking element mounted to the fragment, and a computer coupled to the localization system. The computer measures the change in bone fragment orientation data (CBFOD) from a baseline position to the current position using the reference and tracking elements. Pre-operative planning information is uploaded to the computer, which allows it to map the CBFOD to one or more relevant clinical parameters. The computer system displays the planned and current clinical measurements, allowing a user to target an appropriate fragment position. This system may be used, for example, to reorient a bone fragment during PAO to a new desired position while displaying clinically relevant measurements. An illustration of the user interface 100 for such a system is provided in FIG. 1, showing clinically relevant measurements 102 including lateral center edge angle (LCEA) and anterior center edge angle (ACEA) as they are currently measured (respectively 104 and 106) and at the pre-planned target orientation (respectively 108 and 110). Current and targeted CBFOD is also provided (collectively 112 for both current and target), shown in terms of rotation angles about clinically relevant axes (inclination 112A and 112B, version 112C and 112D and tilt 112E and 112F).

The planning information may be communicated to the computer system in a variety of formats. One format may be the coefficients of a known function, which takes the CBFOD and calculates one or more clinical measurements. The information may also be provided as a look-up-table between the CBFOD and the clinical measurements that may be interpolated as required. Additionally, the planning information may be communicated as 3D anatomic information, such as points on the acetabular rim and the hip center of rotation, and for the computer to use to calculate relevant clinical parameters. The planning information is defined in an anatomic frame of reference (FOR). Examples of this FOR may be the supine coronal plane, or the anterior pelvic plane.

The planning information may be communicated to the computer system using a variety of modes. The information may be encapsulated in an electronic file manually loaded into the computer by the user. An electronic file may be communicated to the computer system through electronic communication such as email, or may be transmitted via a portable electronic storage medium such as a USB drive or external hard drive. Alternatively, the planning information may be stored on a remote server, and the computer may be networked to access the remote server to download the planning information. Another implementation may be to encode the planning information into a physical medium such as a printed QR code, and to have the QR code physically sent to the user. This QR code may be read by an optical reader in the localizer system or the computer system.

If the planning information was communicated as a set of 3D acetabular rim points, the computer may calculate this mapping by rotating the points in 3D according to the CBFOD, and measuring the angle between a line from the hip center to the most lateral rim point, and the patient vertical axis.

Because the planning information is patient specific, it is necessary to communicate some identifying information about the patient along with the file. This information may be included in the data file directly or may be communicated through other means such as electronic communication, such as the subject line in an email, and uploaded or entered separately to the computer at the time of surgery. This information may, for example, be communicated as patient hospital number, or a name.

To calculate the CBFOD, a reference element may be rigidly attached to the bone, and the tracking element may be rigidly attached to the fragment. The position and orientation state estimate (POSE) relative to the localization coordinate system for each element may be calculated. The POSE of the tracking element at a baseline position may be captured and stored by the system, and compared to the POSE after the fragment has been moved. The orientation component of this relative POSE is the CBFOD and is represented in the reference element coordinate system. Additionally, the transformation from the reference element coordinate system to the planning FOR may be determined via an anatomical registration (e.g. may be calculated using anatomic landmarks). If the localizer is an optical tracking system, the reference element may be an element which is trackable by the camera, or it may be the camera itself.

The reference and tracking elements may allow the POSE to be calculated in real time, allowing for real time clinical measurements to be displayed to the surgeon on a screen.

Figure 2:
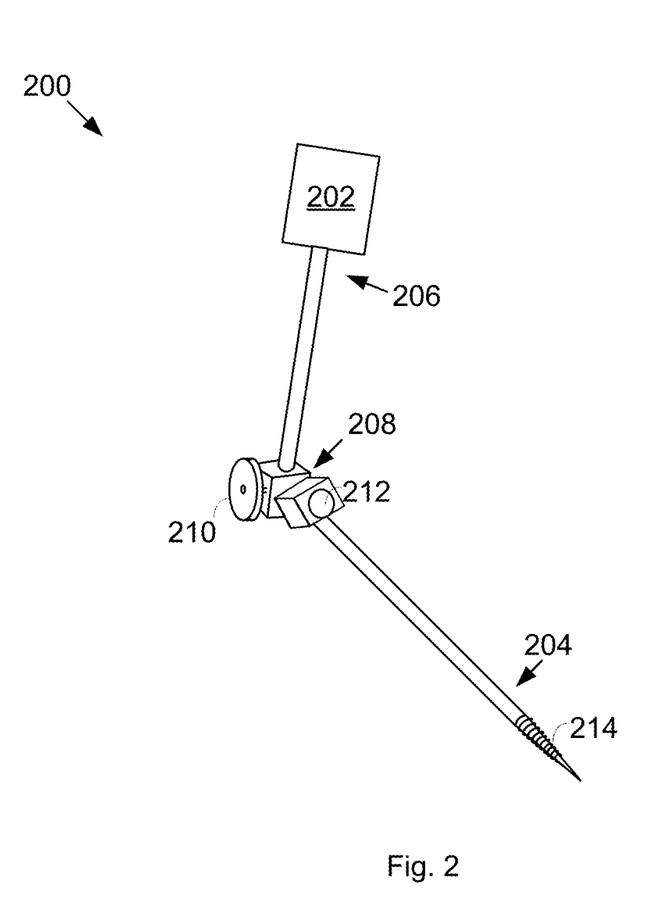
FIG. 2 is an illustration of a tracking element coupling component.

An illustration of a tracking element coupling component 200 is provided in FIG. 2. A tracking element coupling component 200 is required to mount a tracking element 202 on a bone fragment (not shown in FIG. 2). This component 200 has two ends. One end (e.g. a base 204) is configured to mount to the bone, and on the other end 206 (e.g. a free end) may comprise the tracking element 202 which may be tracked by the localizer system or have a quick connect mechanism (not shown) to couple to a removable tracking element. Between the two ends is an adjustment mechanism 208 (e.g. one or more rotation mechanisms with set screws (e.g. 210, 212), etc.) configured to allow one or more degrees of orientation freedom. The adjustment mechanism facilitates 208 the free end and the tracking element 202 thereabout to be repositioned with respect to the base 204. A user may desire to reposition the trackable element 202 after the base 204 has been attached to the bone fragment to increase the localizer system's ability to track the trackable element 202, for example, in the case of line-of-sight issues common with optical localizer systems. The adjustment mechanism 208 may also provide a method to adjust one or more degrees of translation. The tracking element coupling component 200 may also be configured such that the base is detachable from the remainder of the tracking element coupling component such as via a quick connect mechanism (not shown).

Since the baseline position of the fragment is measured before the user has detached it from the bone, the tracking element coupling component is installed prior to the removal of the fragment. In its entirety, this component can often get in the way of the surgeon's tools. To overcome this, when configured with a quick connect base, the majority of the component may be removed, leaving a low-profile base, and later reattached in a repeatable position. The quick connect may be repeatable in 6 degrees of freedom ("6 DOF"). A quick connect mechanism may comprise mating surfaces with cooperative pins/projections and indents or grooves to receive the pins/projections. The cooperative pins/projections and indents or grooves are arranged to receive one another in a repeatable fashion (e.g. a unique combination). A magnet may be used to provide a magnetic attraction to enforce the connection. A quick connect mechanism is shown and described in Applicant's published application, U.S. 20140275940 titled "System and Method for Intra-Operative Leg Position Measurement" filed on Mar. 15, 2013, the entire contents of which are incorporated herein by reference. Quick connect mechanisms may comprise other configurations. A quick connect mechanism is repeatable and accurate to ensure that the pose of the tracking element repeatably and accurately relates to the pose of the bone fragment to which it is attached.

Figure 3A:
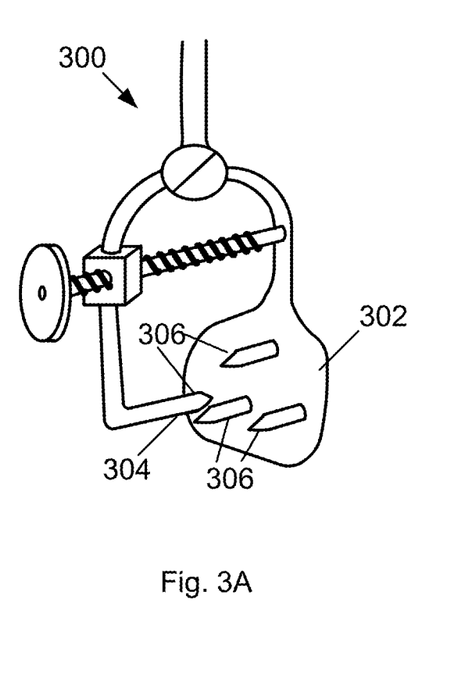
FIGS. 3A and 3B are illustrations of fixation options for a tracking element coupling component.
Figure 3B:
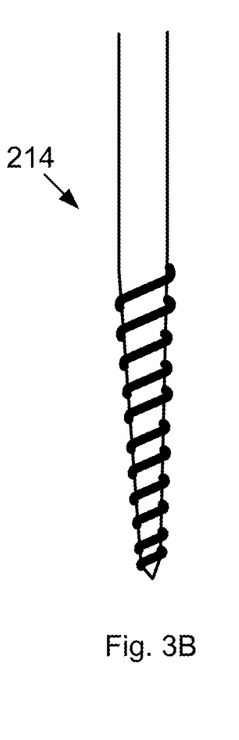

FIG. 2 shows a bone screw configuration 214 at the base 204. However alternate coupling interfaces may be employed for base 204. For example, with reference to FIG. 3A, to attach the tracking element coupling component 200 to the bone fragment, a clamping mechanism 300 (FIG. 3A) may be used to attach to a thin section of the bone fragment. Clamping faces 302, 304 of the clamping mechanism 300 may provide pins or teeth (e.g. 306) which interface with the bone fragment to prevent the clamping mechanism 300 from moving relative to the fragment under the application of force to the tracking element coupling component. This force may be caused by one or more of contact with the patient's soft tissues, the user grabbing on to the tracking element coupling component to move the fragment, or the weight of the tracking element coupling component 200 itself. A clamping mechanism may reduce the risk that the tracking element coupling component 200 is shifted by other hardware, such as the Shantz Pin, or any fragment fixation hardware because it principally resides outside of the bone. That is, the base 204, when implemented as or with a clamping mechanism, derives its rigidity with respect to the bone fragment from the opposing clamping force; teeth may be provided to penetrate the bone fragment for additional stability, but the penetration would be superficial with respect to the bone fragment. Alternatively, the tracking element coupling component 200 may be attached to the bone fragment by means of a fixation screw 214. FIGS. 3A and 3B Illustrate fixation options 300 and 214 for the tracking element coupling component 200 comprising a clamping mechanism (FIG. 3A) and a bone screw 214 in FIG. 3B. It will be understood that FIGS. 3A and 3B are not to the same scale.

In the example of a PAO procedure, the tracking element coupling component 200, with either a clamping mechanism 300 or a bone screw 214 as the fixation mechanism, may be installed in the anterior inferior iliac spine or the iliac wall.

Since the user may wish to combine the teachings herein including the components used at the surgical site with traditional methods such as c-arm radiographs for verification purposes, the use of the tracking element coupling component, tracking element, etc. may obscure important anatomic landmarks in a radiograph. Part (e.g. a base 204) or substantially all of the tracking element coupling component 200 may be manufactured from a radiolucent material to allow these anatomic landmarks to be visible on an intra-operative radiograph.

Computer Implementation

The solution herein may be implemented as a computer method, a computing device and/or system, a computer program product or other patent eligible subject matter. In one example, there is provided a computing system comprising one or more processing units and one or more storage devices coupled thereto. The storage devices may be a non-transitory hardware and/or firmware component such as various types of memory, various types of disks, etc.

The storage devices stores instructions (e.g. software components), which when executed by the one or more processing units configures the operation of the computing system. The computing system may be so configured to perform a method as disclosed herein. The computing system may comprise one computer or more than one computer as described further.

Figure 4:
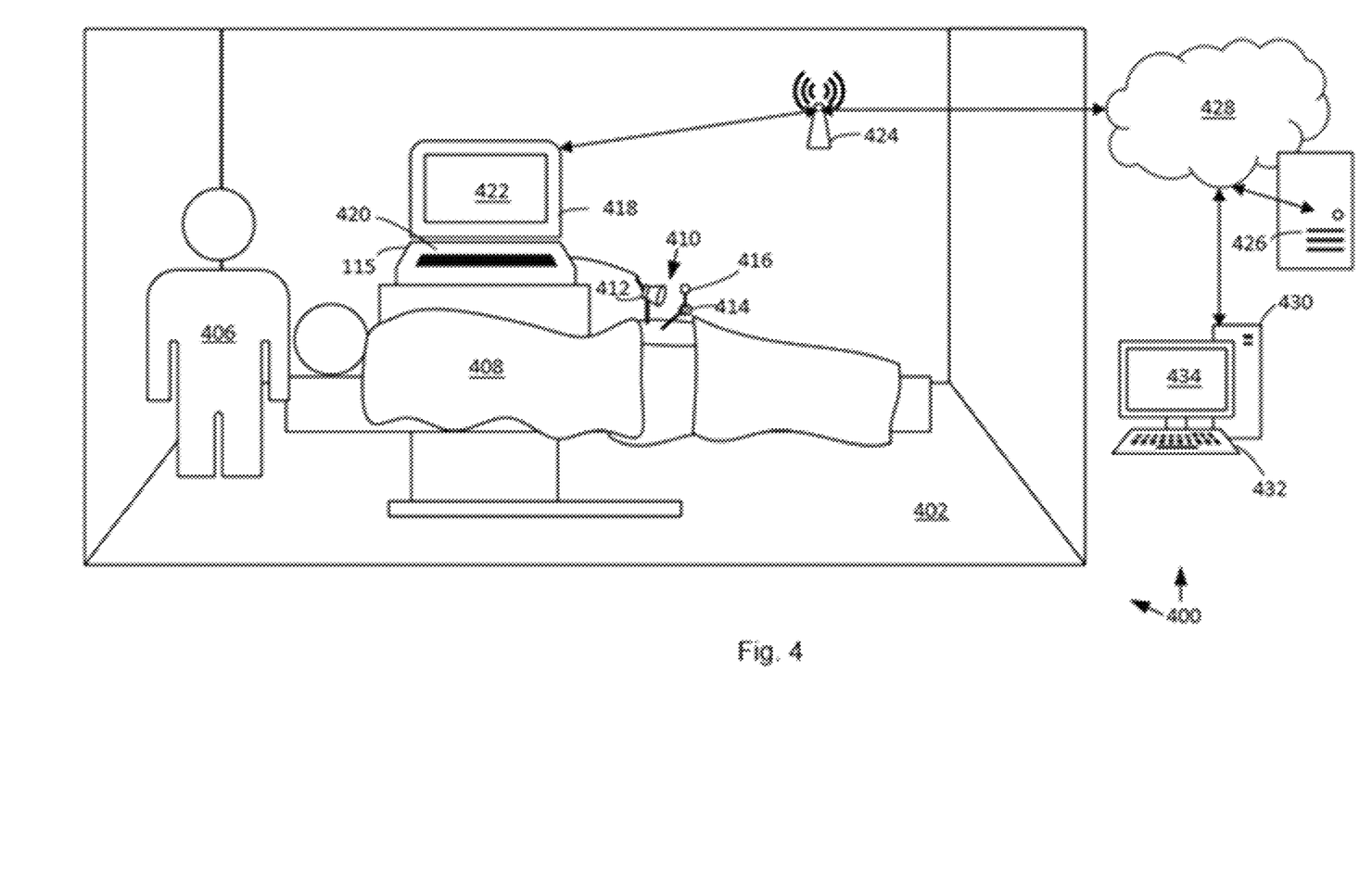
FIG. 4 is an illustration of a computing system in which aspects of the present disclosure may be implanted and/or performed.

FIG. 4 is an illustration of a computing system 400 having components for assisting with surgery as described herein. There is shown an operating room 402 containing a surgeon or other professional (user) 406 and a patient 408. At a surgical site 410 there is located an optical sensor (camera) 412, which may act as a reference element, coupled to the patient's anatomy (e.g. a bone) of the patient 408. Also at site 410 is a tracking element coupling component 414 having a tracking element 416, such as shown with reference to FIGS. 2, 3A and 3B. Tracking element coupling component 414, and thereby tracking element 416, is coupled to a bone fragment of patient 408. Though the present example is shown with a sensor unit that comprises an optical sensor, other non-optical sensor units may be used. The localization system may use magnetic sensing for example.

Optical sensor 412 tracks tracking element 416 optically and provides signals to a localization computer such as intra-operative computing unit 418. Intra-operative computing unit 418 comprises at least one processor unit and at least one storage device (both not shown). The at least one processing unit may be a CPU or other programmable device. Other hardware devices may also be configured (e.g. ASICs, etc.) Storage devices may be memory (RAM, ROM, SRAM, FLASH or other memory) drives (disk, solid state, etc.) and other manners of storing data including instructions.

Intra-operative computing unit 418 comprises or is coupled to at least one input device such as a keyboard 420 and at least one output device such as display screen 422. Optical sensor 412 (as an input device) may be coupled in a wired manner as shown or wirelessly. Optical sensor 412 may carry one or more buttons (not shown) as input devices to computing unit 418. Other input devices that are not shown may include a foot peddle operated button, a microphone, mouse or other pointing device, touch screen input, a second camera such as for reading QR codes, etc.

Output devices not shown may include a speaker, buzzer/bell, lights, etc. Though illustrated as a laptop, other configurations of computing unit 418 will be apparent to those skilled in the art including a workstation, PC, tablet, etc. Intra-operative computing unit 418 also comprises a communication subsystem with one or more units for communication internally and externally. Various wired and wireless technologies may be employed.

Shown is an optional wireless connection to a LAN access point 424, which may couple Intra-operative computing unit 418 to a network accessible computer (e.g. network computing unit 426) via a network 428. Network computing unit 426 may be similarly configured as intra-operative computing unit 418. It may be configured as a server (e.g. having fewer input and/or output devices) to perform operations (e.g. via a server hosted application) for intra-operative computing unit 418.

Also shown is a third computing unit 430 providing a pre-operative computer for planning surgical operations such as described. Third computing unit 430 may be similarly configured viz. components as intra-operative computing unit 418 such as including (e.g. coupled to) input devices such as keyboard 432 and output devices such as display screen 434. Third computing unit 430 may provide data (e.g. pre-operative planning data as described) to network computing unit 426 (which may use such for or provide same to Intra-operative computing unit 418). As previously noted, pre-operative planning data may be communicated to computing unit 418 in other manners such as via a USB device or other portable manner, etc. Intra-operative computing unit 418 may provide such pre-operative data to network computing unit 426. Network computing unit 426 may have access to patient data (not shown) or receive same from intra-operative computing unit 418.

In a configuration, computing unit 418 is an intra-operative computing unit and communicates with network accessible computing unit 426 to receive data therefrom. In some instances, network accessible computing unit 426 receives intra-operative data from intra-operative computing unit 418 (e.g. localization data determined by intra-operative computing unit 418) and performs various computations and/or determinations and returns results to intra-operative computing unit 418 for display intra-operatively. Intra-operative data may include CBFOD, for example. In other instances intra-operative computing unit 418 may be configured to perform the various computations and determinations locally. Intra-operative computing unit 418 may communicate with network accessible computing unit 426 for patient data, pre-planning data or not at all.

Network computing unit 426 may be configured to:
a. receive, e.g. from the intra-operative computing unit, CBFOD;
b. receive mapping information;
c. define the map;
d. compute the clinical parameters based on the map and the CBFOD, and;
e. transmit the clinical parameters to the intra-operative computing for providing for display.

It understood that in some configurations the intra-operative computing unit may perform operations to define the map and determine clinical parameters locally, without using network computing unit 426.

Thus FIG. 4 shows a system for bone reorientation on a patient. The system may include components of the localization system (e.g. reference element and tracking element) and at least one computing unit coupled thereto (e.g. directly such as intra-operative computing unit 418 or indirectly such as network computing unit 426 that receives localization data from intra-operative computing unit 418) for assisting with such a procedure. The at least one computing unit (e.g. the processing unit(s) via instructions from the storage device(s)) may be configured to calculate and provide for display clinical parameters based on a determined CBFOD. In one example, the at least one computing unit may be configured to:
 receive change in bone fragment orientation data (CBFOD) from the localization system;
 receive mapping information to define a map between a CBFOD and clinical parameters; and
 calculate and provide for display clinical parameters based on the CBFOD and the map.

The CBFOD and the mapping information may be with respect to corresponding frames of reference. The mapping information may be generated from a pre-operative medical image of the patient's bone and bone fragment region.

The mapping information may be one of:
a. Coefficients of a function;
b. A look up table; and
c. Data representing 3D anatomical points.

The 3D anatomical points may include the acetabular rim points wherein the bone is a pelvis (for example for peri-acetabular osteotomy (PAO) surgery).

The mapping information may be based on one or more of:
a. radiographic indicators;
b. computer simulation, simulating reorienting the bone fragment of the bone; and
c. target clinical parameters.

The map may be a nonlinear map, where a constant change in the mapping input results in a variable change in the mapping output.

The map may be a many-to-one map, where multiple sets of one or more mapping inputs results in the same set of one or more mapping outputs.

The bone reorientation may be a peri-acetabular osteotomy. In such a case, the bone comprises a pelvis, the bone fragment comprises a native acetabulum, and the clinical parameters include a LCEA and ACEA.

The mapping information is typically defined with respect to an anatomical frame of reference. The reference element initially is defined with respect to its own frame of reference. The two frames of references may be associated (e.g. such as through registration providing correspondence (frame of referenced mapping information). Thus the at least one computing unit may be further configured to register the reference element to the anatomical frame of reference. The anatomical frame of reference may be one of a supine coronal plane and an anterior pelvic plane. Various manners to register the reference element are well known to persons of ordinary skill in the art.

The reference element may comprise an optical sensor (camera) with a field of view oriented toward a surgical site, and the tracker element comprise optically detectable markers for measurement by the camera.

The at least one computing unit may perform operations in real time (i.e. responsive to further changes to bone fragment orientation data).

The at least one computing unit may comprise an intra-operative computing unit and a network computing unit, wherein:
a. Upon receipt, the intra-operative computer transmits the CBFOD to the network-computer unit;

b. the network computing:
  i. receives the mapping information;
  ii. defines the map;
  iii. computes the clinical parameters based on the map and the CBFOD; and
  iv. transmits the clinical parameters to the intra-operative computing unit for providing for display.

The mapping information may be encoded in a QR code and received by the at least one computing unit via a camera device coupled to the at least one computing unit. The QR code may be generated on a mobile device (e.g. smart phone), and displayed on the mobile device alongside or with patient identifier information thereon such that no patient identifier information need be transferred to or received by the computing unit. That is, the computing unit need not receive patient identifying information (PII) for privacy reasons for example. An approved device for receiving PII, such as the smartphone, may receive such PII but not need to transfer same to the computing unit.

The at least one computing unit may be further configured to receive patient identifier information, and to present for display information to identify the patient.

The mapping information may be received via one of:
a. storage media comprising any of a USB key, a CD or other disk, etc.; and
b. a network connection to a remote server.

The system may further comprising a tracking element coupling component comprising a base at a first end, configured to rigidly attach to the bone fragment, and a tracker element interface on a second end. At least the base may be radiolucent.

The tracking element coupling component may be adjustable between the first end and the second end in at least one degree of orientation.

The tracking element coupling component may be comprised of two members where:
a. the first member comprises the first end having the base, wherein the base having a low profile and providing a quick-connect mechanism; and
b. the second member comprises the second end having the tracker element interface, the second member providing a mating quick connect mechanism to the first member.

The second member may include one or more lockable joints proximate to the mating quick-connect mechanism, to orient and fix the second member to avoid interference with soft tissues.

The base may provide two or more teeth for penetration of a cortical bone layer of the bone fragment, and a screw for rigid fixation to the bone fragment.

The base may provide a non-invasive bone clamp comprising teeth on both sides of the clamp, wherein the bone clamp is configured for tightening/loosening, wherein, when tightened on the bone fragment the teeth only penetrate the bone fragment superficially. The bone fragment may be an acetabular fragment, and the bone clamp configured to tighten on either side of an iliac wall of the acetabular fragment.

Figure 5:
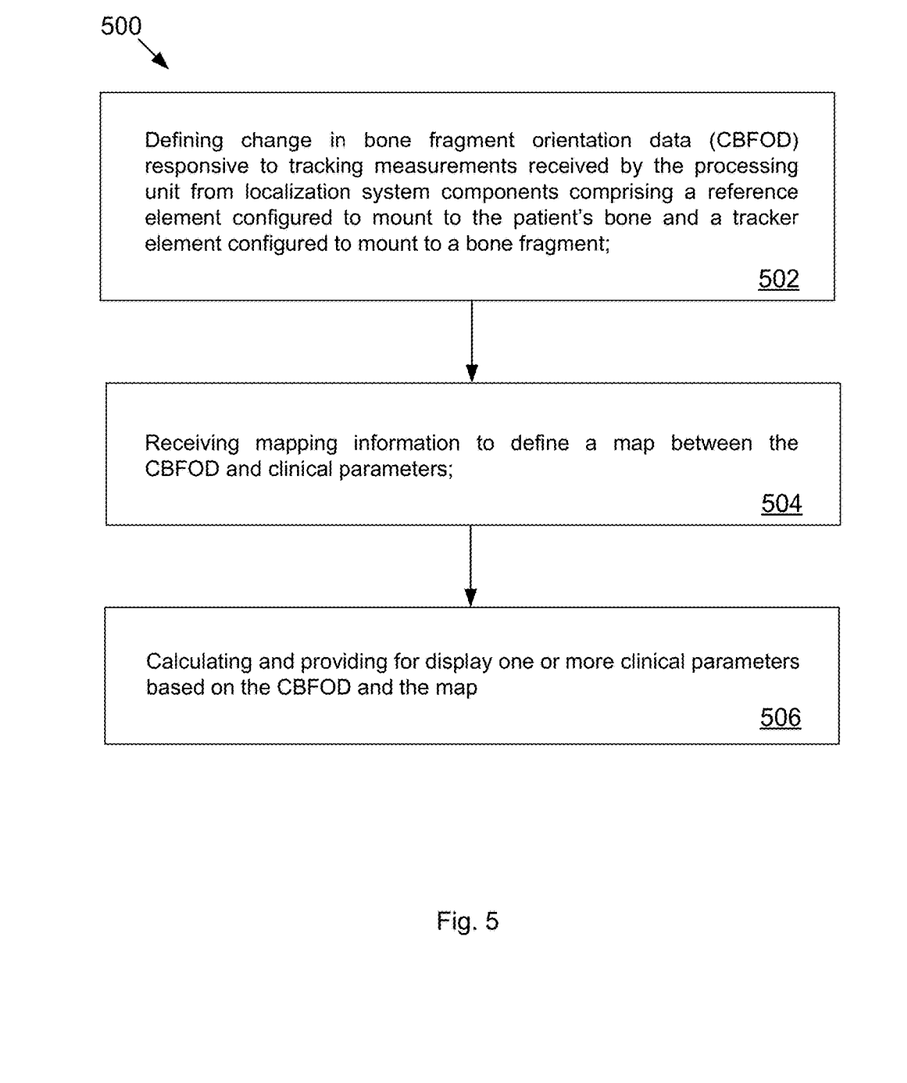
FIGS. 5 and 6 are illustrations of operations of respective methods which may be performed by the systems described herein, including the system of FIG. 4.

FIG. 5 is a flow chart of operations 500 for a method such as for performance by a processing unit of a system such as a system 400. At 502, a processing unit defines change in bone fragment orientation data (CBFOD) responsive to tracking measurements received by the processing unit from localization system components comprising a reference element configured to mount to the patient's bone and a tracker element configured to mount to a bone fragment. At 504 the processing unit receives mapping information to define a map between the CBFOD and clinical parameters. The CBFOD and the mapping information are with respect to corresponding frames of reference; and the mapping information is generated from a pre-operative medical image of the patient's bone and bone fragment region. At 506, the processing unit calculates and provides for display one or more clinical parameters based on the CBFOD and the map.

Figure 6:
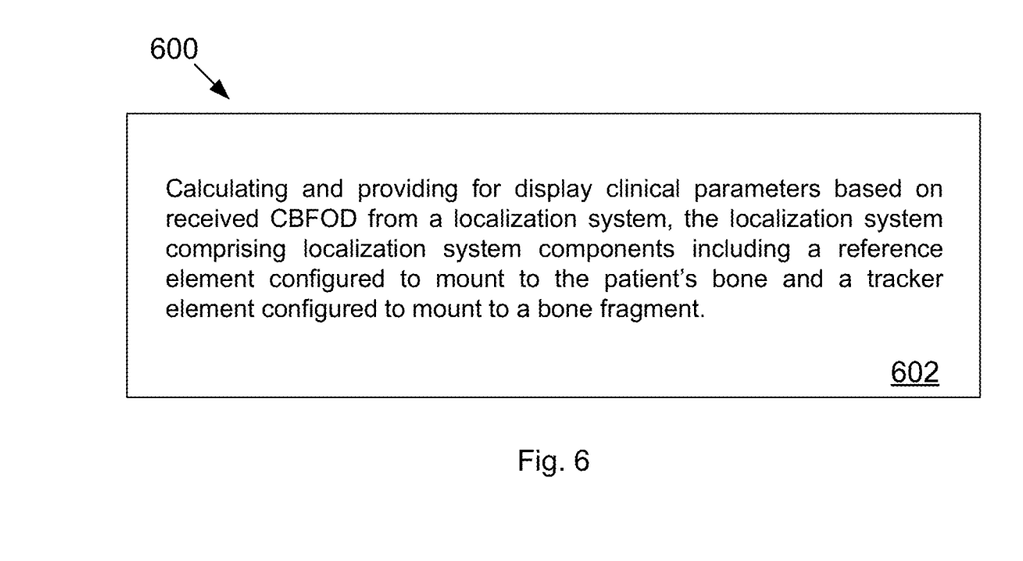

FIG. 6 is a flow chart of operations 600 for a method such as for performance by a processing unit of a system such as a system 400. At 602, the processing unit calculates and provides for display clinical parameters based on received change in bone fragment orientation data (CBFOD) from a localization system, the localization system comprising localization system components including a reference element configured to mount to the patient's bone and a tracker element configured to mount to a bone fragment.

In addition to computing device and system aspects, a person of ordinary skill will understand that computer implemented method and computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A system to perform a bone reorientation on a patient comprising:
   localization system components comprising a reference element to mount to the patient's bone and a tracker element to mount to a bone fragment; and
   at least one computing unit coupled to the localization system components and configured to:
   define change in bone fragment orientation data (CBFOD) responsive to tracking measurements received from the localization system components;
   receive mapping information to define a map between the CBFOD and clinical parameters;
   wherein the CBFOD and the mapping information are with respect to corresponding frames of reference; and
   wherein the mapping information is generated from a pre-operative medical image of the patient's bone and bone fragment region; and
   calculate and provide for display one or more clinical parameters based on the CBFOD and the map;
   wherein:
   the reference element comprises one of i) an optical sensor with a field of view oriented toward a surgical site, or a magnetic sensor with a field of view oriented toward the surgical site;
   and ii) a detectable marker for measurement by one of the optical sensor or the magnetic sensor;
   the tracking element comprises a detectable marker for measurement by one of the optical sensor or the magnetic sensor;
   the computing unit comprises a processor;
   the bone reorientation is a peri-acetabular osteotomy, the bone is a pelvis, the bone fragment is a native acetabulum; and
   the one or more clinical parameters include a lateral center edge angle (LCEA) and an anterior center edge angle (ACEA).

2. The system of claim 1, wherein the mapping information is one of:
   coefficients of a function, which function calculates a clinical parameter from the CBFOD;
   a look up table; and
   data representing 3D anatomical points.

3. The system of claim 2, wherein the 3D anatomical points include acetabular rim points and wherein the patient's bone is a pelvis.

4. The system of claim 1, wherein the at least one computing unit is further configured to receive patient identifier information, and to present for display information to identify the patient.

5. The system of claim 1, wherein the mapping information is based on one or more of:
   radiographic indicators;
   computer simulation, simulating reorienting the bone fragment of the bone; and
   target clinical parameters.

6. The system of claim 1, wherein the map comprises a nonlinear map, where a constant change in the mapping input results in a variable change in the mapping output.

7. The system of claim 1, wherein the map comprises a many-to-one map, where multiple sets of one or more mapping inputs results in the same set of one or more mapping outputs.

8. The system of claim 1, wherein the reference element is the magnetic sensor and the tracking element comprise the detectable marker for measurement by the magnetic sensor.

9. The system of claim 1, wherein the mapping information is defined with respect to an anatomical frame of reference and wherein the at least one computing unit is further configured to register the reference element to the anatomical frame of reference.

10. The system of claim 9, wherein the anatomical frame of reference is one of a supine coronal plane and an anterior pelvic plane.

11. The system of claim 1, wherein the reference element is the optical sensor, and the tracker element comprises the detectable marker for measurement by the optical sensor.

12. The system of claim 1, wherein the at least one computer unit is configured to perform operations in real time responsive to further changes to bone fragment orientation data.

13. The system of claim 1, wherein the at least one computing unit comprises an intra-operative computing unit and a network computing unit coupled for communication via a network, wherein:
   the intra-operative computing unit transmits the CBFOD to the network computing unit; and
   the network computing unit:
   i. receives the mapping information;
   ii. defines the map;
   iii. computes the one or more clinical parameters based on the map and the CBFOD; and
   iv. transmits the one or more clinical parameters to the intra-operative computer for providing for display.

14. The system of claim 1, wherein the mapping information is encoded in a quick response (QR) code and received by the at least one computing unit via a camera device coupled to the at least one computing unit.

15. The system of claim 14, wherein the QR code is generated on a mobile device for presenting to the computing unit and displayed along with patient identifier information such that no patient identifying information is transferred to the computing unit.

16. The system of claim 1, wherein the mapping information is received via one of:
   a storage media; and
   a network connection to a remote server.

17. A computer-implemented method to perform a bone reorientation on a patient comprising:
   defining, by a processing unit, change in bone fragment orientation data (CBFOD) responsive to tracking measurements received by the processing unit from localization system components comprising a reference element configured to mount to the patient's bone and a tracker element configured to mount to a bone fragment;
   receiving, by the processing unit, mapping information to define a map between the CBFOD and clinical parameters;
   wherein the CBFOD and the mapping information are with respect to corresponding frames of reference; and
   wherein the mapping information is generated from a pre-operative medical image of the patient's bone and bone fragment region; and
   calculating and providing for display, by the processing unit, one or more clinical parameters based on the CBFOD and the map;
   wherein:
   the reference element comprises one of i) an optical sensor with a field of view oriented toward a surgical site, or a magnetic sensor with a field of view oriented toward the surgical site;

and ii) a detectable marker for measurement by one of the optical sensor or the magnetic sensor;

the tracking element comprises a detectable marker for measurement by one of the optical sensor or the magnetic sensor;

the processing unit comprises a processor;

the bone reorientation is a peri-acetabular osteotomy, the bone is a pelvis, the bone fragment is a native acetabulum; and the one or more clinical parameters include a lateral center edge angle (LCEA) and an anterior center edge angle (ACEA).

18. The method of claim 17, wherein the mapping information is one of:

coefficients of a function, which function calculates a clinical parameter from the CBFOD;

a look up table; and data representing 3D anatomical points.

19. The method of claim 18, wherein the 3D anatomical points include acetabular rim points and wherein the patient's bone is a pelvis.

20. The method of claim 17 comprising receiving, by the processing unit, patient identifier information and presenting the patient identifier information for display to identify the patient.

21. The method of claim 17, wherein the reference element is the optical sensor and the tracker element comprises the detectable marker for measurement by the optical sensor.

\* \* \* \* \*